United States Patent [19]

Lange et al.

[11] 4,021,541

[45] May 3, 1977

[54] ANTIGEN ISOLATED FROM GROUP A (BETA-HEMOLYTIC) STREPTOCOCCI AND METHOD FOR ISOLATING THE SAME

[75] Inventors: Kurt Lange, New York; Gerhard Treser, Thornwood, both of N.Y.

[73] Assignee: New York Medical College, New York, N.Y.

[22] Filed: Oct. 20, 1975

[21] Appl. No.: 624,266

[52] U.S. Cl. ................................................ 424/92
[51] Int. Cl.² ...................................... A61K 39/02
[58] Field of Search ...................................... 424/92

[56] References Cited
UNITED STATES PATENTS 3,810,819  5/1974  Okamoto et al. ..................... 195/4

OTHER PUBLICATIONS

Okamoto et al.—Chem. Abst.—vol. 81 (1974), p. 11842z.

*Primary Examiner*—Sam Rosen
*Attorney, Agent, or Firm*—Flynn & Frishauf

[57] ABSTRACT

An antigen, a water-soluble protein, is isolated from group A (beta-hemolytic) streptococci by suspending the streptococci in an aqueous medium and subjecting the resulting mixture to disintegration by various means whereby the streptococci cells are disrupted. The supernatant contains the antigen, which can be purified by fractionation, particularly chromatographic adsorption.

10 Claims, No Drawings

ANTIGEN ISOLATED FROM GROUP A (BETA-HEMOLYTIC) STREPTOCOCCI AND METHOD FOR ISOLATING THE SAME

The invention described herein was made in the course of work under a grant or award from the Department of Health, Education and Welfare.

This invention relates to discovery of an antigen isolated from group A (beta-hemolytic) steptococci, and to a method for isolating the same.

It is generally agreed that group A streptococci are the cause of most cases of acute glomerulonephritis. It is also generally accepted that acute poststreptococca glomerulonephritis is the consequence of a complement-binding antigen-antibody reaction. During the early phase of the streptococcal infection, glomerular basement membranes are only partially covered with antibody (IgG) and complement ($\beta$1C). After about 10 days, all basement membranes and parts of the mesangial areas are covered with antibody and complement. It has been found that the antibody in glomerulonephritis is directed against an antigen which is only present in unsaturated form in the first few days of the disease and then becomes rapidly saturated with antibody and can no longer be detected by labelled specific antibody.

As indicated, the antigen appears to be related to acute poststreptococcal glomerulonephritis (AGN) where it produces an antibody reaction possibly leading to the disease process. Yet, an antibody against this substance may be present in many "normal" individuals who may have been exposed to minimal amounts of this antigen leading to antibody-formation, but not necessarily to disease or only to a mild form of disease which usually escapes clinical detection.

From prior research, it appears that the antigen is present initially subendothelially and in the mesangium not saturated with antibody. It cannot penetrate the barrier layer of the basement membrane until it is complexed with antibody and complement, the latter increasing the permeability of the basement membrane, and permitting permeation of the immune complexes into and through the membrane eventually forming subepithelial immune aggregates. It appears that the antigen is unable to penetrate the barrier layer because of its molecular size. Further, it attracts its own specific antibody when the latter becomes available, complexes are formed directly under the basement membrane and complement-induced membrane alterations and penetration of the immune complexes result.

The antigen seems to be common to most, if not all, group A streptococci according to Lancefield's classification (Harvey Lect. 36: 251, 1940). Further, the antigen is liberated only when streptococci are disrupted. It does not appear to be an exozyme which would be excreted by the streptococci so long as they are intact.

Prior efforts to isolate the antigen efficiently and in relatively high concentration have been unsatisfactory (Treser, G.; Semar, M.; Ty, A.; Sagel, I.; Franklin, M.A.; and Lange, K.; J. Clin. Invest. 49: 762, 1970). For example, group A streptococci isolated from patients having a AGN were grown for 20 hours at 37° C in a suitable medium, the medium was then removed and the cells were washed with physiological saline and in a phosphate buffer. The intact streptococci were disrupted by freezing-thawing five times in a dry ice-acetone mixture, in order to disrupt the cells and obtain a supernate and obtain cell fractions. This method has proved to be disadvantageous because of small yields.

There is, therefore, a need for an efficient method for isolating an antigen from group A streptococci in relatively large quantities and high concentration.

SUMMARY OF THE INVENTION

In accordance with the provision of this invention, there is provided an antigen isolated from group A streptococci and a method for isolating the same.

The antigen is a protein and is characterized by particular properties, and by the absence of certain characteristics, as explained hereinafter.

The method comprises suspending group A streptococci in an aqueous medium and applying mechanical energy to the resulting mixture, while maintaining the temperature of said mixture below 70° C, and separating the resultant supernatant containing the desired antigen and resulting water-insoluble cell constituents.

EMBODIMENTS OF THE INVENTION

As indicated above, group A streptococci are suspended in water of about neutral pH.

Mechanical energy is then applied to the resulting mixture, care being taken that the temperature of the medium does not exceed 70° C. Generally the temperature will be approximately 30° C.

Mechanical energy can be applied to the resulting mixture by placing the mixture in a pressure vessel, pressurizing the vessel to from about 20,000 to about 50,000 pounds per square inch (psi), and then suddenly (abruptly) releasing the pressure to atmospheric. As indicated above, this must be conducted such that the temperature of the resulting mixture remains below 70° C. Proper control of the temperature can be accomplished by having a suitable coolant in walls of the vessel for indirect heat exchange with the mixture. Typical equipment for this purpose is RF-1 Sorvall-Ribi refrigerated cell fractionator.

An alternate, but less advantageous, means for disrupting the streptococci is ultrasonic vibration. Here again, denaturation by excessive temperatures (above 70° C) is to be avoided. A typical source of ultrasonic vibrations is an Ultrasonifer, of Heat Systems Ultrasonic Inc., Model W140D, which has a maximum output of 20,000 cycles per second for 10 minutes.

The resulting supernatant and resulting waterinsoluble cell fragments are then separated. The super-natent contains the antigen.

Column chromatography with Bio-Gel A5m, 100–200 mesh, fractionation range of 10,000–5,000,000, agarose concentration 6%; Sepharose 6B, fractionation range of $10^5$ to $4\times10^6$, agarose concentration 6%; or other suitable media, can be employed to fractionate the supernatent obtained by the method of this invention. The activity which preabsorbs the antibody out of staining sera of patients convalescing from AGN is then confined to one or a few successive tubes of eluate while subsequent fractions cannot produce such an effect.

Similarly, when a supernatent is subjected to acrylamide gel electrophoresis, only a small area near the anode contains the preabsorbing substance. Thus, these and other similar methods permit further purification of the substance.

The substance, when opposed in Agarose double immuno-diffusion plates to sera of patients convalescing from AGN, reacts with formation of a precipitin line.

As indicated above, the antigen is a protein. It is characterized by the following properties and by the absence of certain characteristics:

water soluble;

not inactivated by exposure to changes in pH between 3 and 9;

activity is destroyed by heating to 70° C and above;

not dialyzable through a semi-permeable membrane;

does not contain free nucleic acids (not precipitated by streptomycin sulfate);

not inactivated by ribonuclease or desoxyribonuclease;

precipitates by 60% saturation with $(NH_4)_2SO_4$ solution;

does not react with 3,5-dihydroxytoluene (Orcinol);

not immunologically identical with steptolysin, streptodornase, streptokinase or hyaluronidase as shown by non-identity with the precipitin lines between these substances and the serum of a patient convalescing from AGN and the precipitin line formed between the antigen and the patient's serum.

The antigen readily produces antibodies when injected into rabbits or other suitable hosts. Immunologically identical antibodies to this antigen can be found in the serum of patients convalescing from AGN, and as mentioned before, also in normal individuals.

Immune gamma globulin in sera of patients convalescing from AGN when labelled with fluorescein will stain sites on glomeruli obtained from patients with glomerulonephritis during the early phase of the disease indicating the presence of free antigen. When such sera are previously preabsorbed with the streptococcal substances described herein, they will not stain the glomeruli any longer since the streptococcal substance apparently contains the antigen which reacts with the antibody in the serum of patients convalescing from AGN.

The antigen can serve to classify streptococci, since group A (beta-hemolytic) steptococci which are nephritogenic, i.e., produce acute glomerulonephritis in a suitable host, seem to carry the substance exclusively or at least in greater amounts than non-nephritogenic group A streptococci. The substance could be used to determine the nephritogenicity of group A streptococci.

If this antigen is, as it appears to be, the antigen causing acute poststreptococcal glomerulonephritis (AGN), injection of small amounts of the substance may prove to be suitable to be used as a vaccine, producing protective antibodies without producing disease.

Illustrative, non-limiting examples of the invention are set forth below.

EXAMPLE 1

Strains of group A ($\beta$-hemolytic) streptococci belonging to various M types and T types are isolated from patients with acute poststreptococcal glomerulonephritis or patients with group A streptococcal infections. The streptococci are grown in 8–12 liters of Todd-Hewitt broth for 18 hours and harvested by the continuous flow system of a Sorvall RC-2 centrifuge (Ivan Sorvall, Inc., Norwalk, Conn.). The sedimented cells are washed three times with phosphate buffered saline, pH 7.2 (PBS). After suspending the washed cells in an appropriate volume of distilled water, they are disrupted by explosive decompression in the Ribi cell fractionator (Ivan Sorvall, Inc., Norwalk, Conn.) at a pressure of 35,000 p.s.i. The cell suspension is centrifuged at 16,000 r.p.m. for one hour in a refrigerated centrifuge. The sediment obtained is washed three times each with PBS and distilled water (d.w.) and lyophilized. The supernatant, from now on referred to as RCS (ruptured streptococcal cell supernatants) provides the working material.

Nucleic acids are removed from the RCS by the addition of one part of 0.2M streptomycin sulfate (Calbiochem, San Diego, Calif.) to nine parts of the RCS. The mixture is incubated for 2 hours at 4° C and the precipitated nucleic acids are removed by centrifugation at 12,000 r.p.m. for 30 minutes. The clear RCS is dialyzed thoroughly against D.W. and lyophilized. The RCS is precipitated by 60% saturation with ammonium sulfate. The precipitate is dissolved in water a second time at the same saturation of ammonium sulfate and precipitated again. This precipitate is dissolved in PBS and dialyzed overnight against the same buffer.

The presence of the antigen in the streptococcal RCS is demonstrated by an absorption technique. 1.0 mg of lyophilized RCS or of other fractions to be tested is added to 0.1 ml of the fluorescein isothiocyanate-labelled immunoglobulin G fractions of ser under study. When intact sedimented bacteria are used for preabsorption equal and larger amounts are employed. The mixture is incubated at 37° C for 1 hour and overnight at 4° C. The insoluble material is removed by centrifugation at 12,000 r.p.m. for 30 minutes and the clear solutions are used for staining the kidney sections. If the labelled sera stain kidney biopsies of patients with early acute poststreptococcal glomerulonephritis, they contain an antibody against certain parts of the biopsy. If these sera, however, do not stain the kidney biopsies any longer after the streptococcal supernate or its fractions are added, preabsorption of the staining antibody has taken place by an antigen, indentifying it as immunologically identical with the antigen on the kidney biopsy.

EXAMPLE 2

The lyophilized material obtained as described in Example 1 is used for further purification by column chromatography. Bio-Gel A-5 (Bio-Rad Laboratories, Rockville Center N.Y. preswollen and suspended in a solution containing 0.02% sodium azide + 0.001 M tris + 0.001 M EDTA is employed in the preparation of a 2.5+ 100 cm column. 0.1 M tris buffer (Trishydroxymethylamino methane and HCl) pH 7.2 is used for packing the column and as the eluting fluid. 300 mg of ammonium sulfate precipitated RCS are applied to the columm. Flow rates should be of the order of 20–24 ml/hr. Fractions of 4.0 ml are collected with the use of an automatic fraction collector. The fractions are analyzed for protein. One fraction or pools of the purified lyophilized bacterial fractions are dialyzed against distilled water and lyophilized. The purified lyophilized material is then tested for antigenic activity as described in Example 1.

EXAMPLE 3

The lyophilized material obtained as desribed in Example 1 is subjected to analytical electrophoresis on polyacrylamide gel (75% gel) as described by Davis (Davis, B. J. Ann N.Y. Acad. Sci. 121: 404–427, 1964). Samples of 300 μg are applied. Protein hands are detected by staining the gels with 0.1% solution of Amido Black in 7% acetic acid for one hour followed by destaining in 7% acetic acid. For elution studies, numerous polyacrylamide columns are produced simultaneously under identical conditions and one of them is stained with Amido Black. The corresponding bands are excised, pooled, minced, shaken for 1 hours at room temperature and filtered through Whatman No. 1 filter paper. The filtrate is dialyzed against several changes of distilled water and lyophilized. This material is used for preabsorption as described in Example 1 thus leading to an isolation of a more purified antigenic substance.

We claim:

1. The method for isolating a water-soluble substance from group A (beta-hemolytic) streptococci, said substance reacting immunologically with antibodies in the serum of a patient convalescing from acute glomerulonephritis and with antibodies of humans who have had previous exposure to group A streptococci and further characterized by the following properties and characteristics:

not inactivated by exposure to changes in pH between 3 and 9;
activity is destroyed by heating to 70° C. and above;
not dialyzable through a semi-permeable membrane;
does not contain free nucleic acids (not precipitated by streptomycin sulfate);
precipitates by 60% saturation with $(NH_4)_2SO_4$ solution;
does not react with 3,5-dihydroxytoluene (Orcinol);
not inactivated by ribonuclease or desoxyribonuclease;
not immunologically identical with streptolysin, streptodornase, streptokinase or hyaluronidase as shown by non-identity with the precipitin lines between these substances and the serum of a patient convalescing from AGN and the precipitin line formed between the antigen and the patient's serum;

said method comprising the sequence of steps:

a. dispersing said group A streptococci in water of about neutral pH;
b. applying mechanical energy to the resulting mixture of (a) by pressuring the resulting mixture and abruptly reducing the pressure thereof or by subjecting the resulting mixture to ultrasonic vibration, while maintaining the temperature of the resulting mixture below 70° C., thereby disrupting cells of said streptococci;
c. separating the resulting supernatant containing said substance and resulting water-insoluble cell fragments, and
d. recovering said water-soluble substance from the supernatent of (c).

2. The method of claim 1, wherein said water-soluble substance is recovered from the supernatent of (c) by e. removing nucleic present in said supernatent therefrom;
f. dialyzing the nucleic acid-free super-natant with distilled water and lyophilizing;
g. forming a precipitate of the lyophilized material obtained in (f) at a 60% saturated ammonium sulfate concentration, and collecting the resulting precipitate.

3. The method of claim 2, wherein said water-soluble substance obtained as a precipitate in (g) is h. dissolved in water and precipitated again at a 60% saturated ammonium sulfate concentration;
i. the precipitate obtained in (h) is dissolved in a phosphate buffered saline, pH 7.2, and dialyzed against said buffer.

4. The method of claim 1, wherein mechanical energy is applied by pressurizing the resulting mixture to a pressure of from about 20,000 to about 50,000 pounds per square inch before the pressure is so reduced.

5. The method of claim 1, wherein mechanical energy is applied by pressurizing the resulting mixture to a pressure of about 35,000 pounds per square inch before the pressure is so reduced.

6. The method of claim 1, wherein mechanical energy is applied by subjecting the resulting mixture to ultrasonic energy of about 20,000 cycles per second.

7. The method of claim 1, wherein the temperature in (b) is about 30° C.

8. The method of claim 1, wherein said supernatant is contacted with a chromatographic media to provide an eluate containing said water-soluble substance.

9. The method of claim 1, wherein the supernatant is fractionated by acrylamide-electrophoresis to obtain a specific band of high concentration of said substance.

10. A water-soluble substance isolated from group A (beta-hemolytic) streptococci by the method of claim 11, and which reacts immuniologically with antibodies in the serum of a patient convalescing from acute glomerulonephritis and with antibodies of humans who have had previous exposure to group A streptococci, further characterized by the following properties and characteristics:

not inactivated by exposure to changes in pH between 3 and 9;
activity is destroyed by heating to 70° C. and above;
not dialyzable through a semi-permeable membrane;
does not contain free nucleic acids (not precipitated by streptomycin sulfate);
precipitates by 60% saturation with $(NH_4)_2SO_4$ solution;
does not react with 3,5-dihydroxytoluene (Orcinol);
not inactivated by ribonuclease or desoxyribonuclease;
not immunologically identical with streptolysin, streptodornase, streptokinase or
hyaluronidase as shown by non-identity with the precipitin lines between these substances and the serum of a patient convalescing from AGN and the precipitin line formed between the antigen and the patient's serum.

* * * * *

UNITED STATES PATENT AND TRADEMARK OFFICE
CERTIFICATE OF CORRECTION

PATENT NO. :    4,021,541
DATED       :    May 3, 1977
INVENTOR(S) :   KURT LANGE et al

It is certified that error appears in the above-identified patent and that said Letters Patent are hereby corrected as shown below:

Column 2, lines 46 and 47: rewrite "supernatent" (line 46) and "super-natent" (line 47) as ---supernatant---.

Column 2, line 46: rewrite "waterinsolu-" as ---water-insolu- ---.

Column 4, line 46: after "N.Y.", insert --- ) ---.

Column 5, line 6: rewrite "hours" as ---hour---.

Column 6, line 36 (Claim 10): replace "11" with ---1---

Signed and Sealed this

Seventeenth Day of June 1980

[SEAL]

Attest:

SIDNEY A. DIAMOND

Attesting Officer

Commissioner of Patents and Trademarks